(12) United States Patent
Fogarty et al.

(10) Patent No.: US 8,133,248 B2
(45) Date of Patent: *Mar. 13, 2012

(54) METHODS AND DEVICES FOR BLOOD VESSEL HARVESTING

(75) Inventors: Thomas J. Fogarty, Portola Valley, CA (US); Kenneth H. Mollenauer, Santa Clara, CA (US); Michelle Y. Monfort, Los Gates, CA (US); George D. Hermann, Los Gates, CA (US); Allan R. Will, Atherton, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 125 days.

This patent is subject to a terminal disclaimer.

(21) Appl. No.: 12/550,462

(22) Filed: Aug. 31, 2009

(65) Prior Publication Data

US 2010/0049235 A1    Feb. 25, 2010

Related U.S. Application Data

(60) Continuation of application No. 11/019,889, filed on Dec. 22, 2004, now Pat. No. 7,588,584, which is a division of application No. 10/244,330, filed on Sep. 16, 2002, now Pat. No. 6,840,946, which is a continuation of application No. 09/520,308, filed on Mar. 7, 2000, now Pat. No. 6,451,035, which is a continuation of application No. 09/236,266, filed on Jan. 22, 1999, now Pat. No. 6,068,639, which is a continuation of application No. 09/145,148, filed on Sep. 1, 1998, now Pat. No. 5,899,913, which is a continuation of application No. 08/991,425, filed on Dec. 15, 1997, now Pat. No. 5,853,417, which is a continuation of application No. 08/475,137, filed on Jun. 7, 1995, now Pat. No. 5,730,748.

(51) Int. Cl.
*A61M 29/00* (2006.01)
(52) U.S. Cl. ...................................................... 606/190
(58) Field of Classification Search .................. 606/190, 606/192, 159, 166, 207, 194; 604/96.01–99.01, 604/103.01–103.04
See application file for complete search history.

(56) References Cited

U.S. PATENT DOCUMENTS 2,944,522 A    7/1960    Cannon
(Continued)

FOREIGN PATENT DOCUMENTS

EP    0 573 273 A2    12/1993
(Continued)

OTHER PUBLICATIONS

European Search Report for corresponding EP 96945432; date of mailing is Jul. 27, 2009; (3 pages).

(Continued)

*Primary Examiner* — Kevin T Truong

(57) ABSTRACT

Methods and devices for harvesting veins from the body. The methods and devices allow vein harvesting using laparoscopic procedures. A working space is created over the vein using standard laparoscopic procedures and a side-hooked wire is inserted into the working space and twisted to insert the side-hook under the vein. The wire is then pulled or drawn along the vein to separate the vein from the surrounding tissue. In an alternative embodiment, vein separation is accomplished by threading a soft rubber tube under the vein, grasping the ends of the tube so as to surround the vein, and then pulling the tube along the vein. In other embodiments, the working space is created with everting balloons.

13 Claims, 9 Drawing Sheets

U.S. PATENT DOCUMENTS

| | | | |
|---|---|---|---|
| 4,271,839 A | | 6/1981 | Fogarty et al. |
| 4,469,100 A | | 9/1984 | Hardwick |
| 4,479,497 A | | 10/1984 | Fogarty et al. |
| 4,493,711 A | | 1/1985 | Chin et al. |
| 4,597,389 A | | 7/1986 | Ibrahim et al. |
| 4,606,347 A | * | 8/1986 | Fogarty et al. ............ 606/194 |
| 4,793,346 A | | 12/1988 | Mindich |
| 4,946,440 A | * | 8/1990 | Hall ............................ 604/164.09 |
| 5,041,089 A | | 8/1991 | Mueller et al. |
| 5,346,503 A | | 9/1994 | Chow |
| 5,352,219 A | | 10/1994 | Reddy |
| 5,359,995 A | | 11/1994 | Sewell, Jr. |
| 5,366,478 A | | 11/1994 | Brinkerhoff et al. |
| 5,373,840 A | | 12/1994 | Knighton |
| 5,397,333 A | | 3/1995 | Knoepfler |
| 5,423,842 A | | 6/1995 | Michelson |
| 5,445,632 A | | 8/1995 | Blake et al. |
| 5,445,990 A | | 8/1995 | Yook et al. |
| 5,480,379 A | | 1/1996 | La Rosa |
| 5,522,824 A | | 6/1996 | Ashby |
| 5,575,759 A | | 11/1996 | Moll et al. |
| 5,591,183 A | | 1/1997 | Chin |
| 5,593,418 A | | 1/1997 | Mollenauer |
| 5,601,581 A | | 2/1997 | Fogarty et al. |
| 5,601,589 A | | 2/1997 | Fogarty et al. |
| 5,611,814 A | | 3/1997 | Lorenc |
| 5,632,761 A | | 5/1997 | Smith et al. |
| 5,667,480 A | | 9/1997 | Knight et al. |
| 5,730,748 A | | 3/1998 | Fogarty et al. |
| 5,762,604 A | | 6/1998 | Kieturakis |
| 5,772,680 A | | 6/1998 | Kieturakis et al. |
| 5,846,256 A | | 12/1998 | Mathis et al. |
| RE36,043 E | | 1/1999 | Knighton |
| 5,860,997 A | | 1/1999 | Bonutti |
| 7,588,584 B2 | * | 9/2009 | Fogarty et al. ............ 606/190 |

FOREIGN PATENT DOCUMENTS

WO    WO 97/13464    4/1997

OTHER PUBLICATIONS

"SaphLITE™ Saphenous Vein System" Copyright 1998—Genzyme Surgical Products, Apr. 1998 (4 pages).

"Endoscopic Subfascial Discission of Perforating Veins" (G. Hauer et al., Surg. Endosc. (1988) 2:5-12).

"Long Saphenous Vein Harvesting" (W. Meldrum-Hanna et al., Aust. N.Z.J. Surg. 1986, 923-924).

"Vein Harvest" Alan B. Lumaden & Gelmont Faves III, Endoscopic Plastic Surgery (Quality Medical Publishing, Inc. 1995), pp. 535-543.

"Endoscopic Plastic Surgery" Snowden-Pencer, Incs. (1993 Brochure).

"A quick and atraumatic method of autologus vein harvesting using the subcataneous extraluminal dissector" (W.R. Dimitri et al., J. Cardiovasc Surg., 1987; 28:103-11).

* cited by examiner

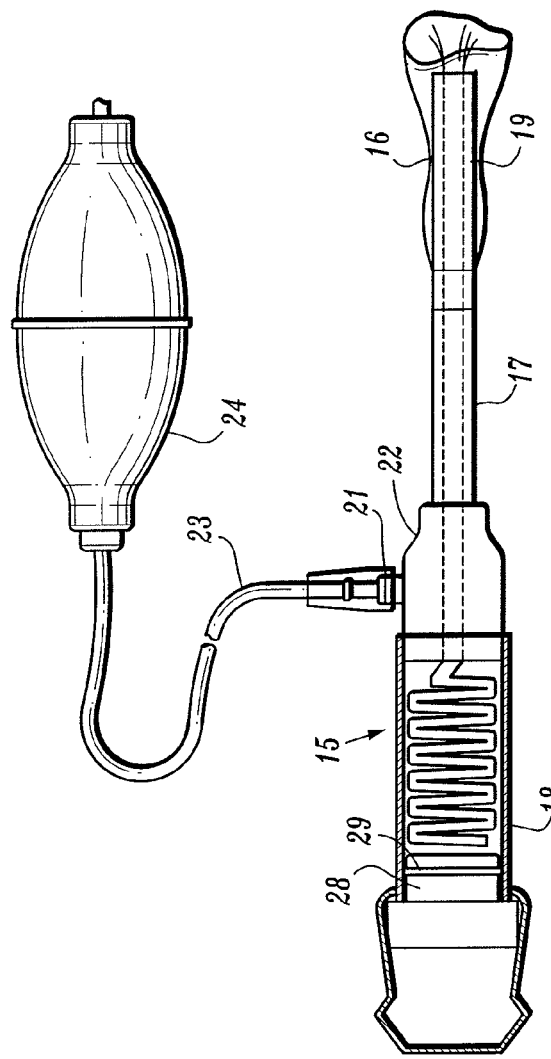
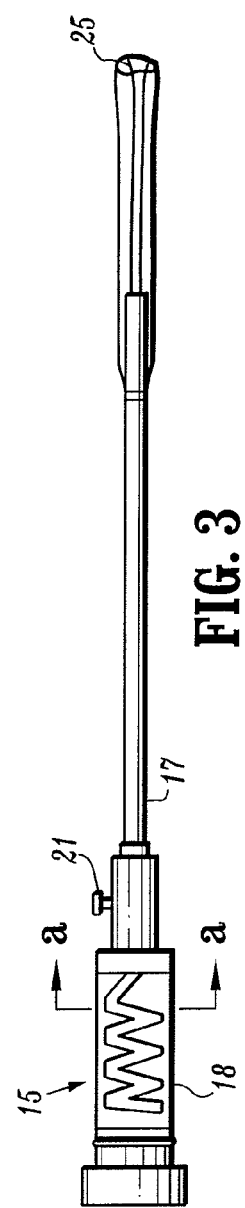
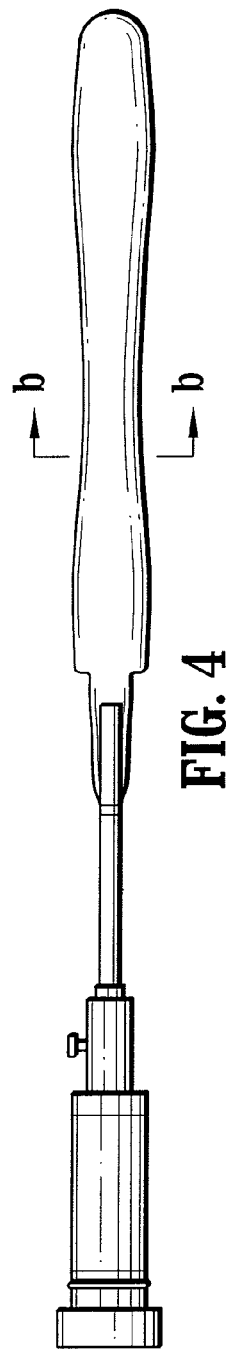
FIG. 2
FIG. 3
FIG. 4

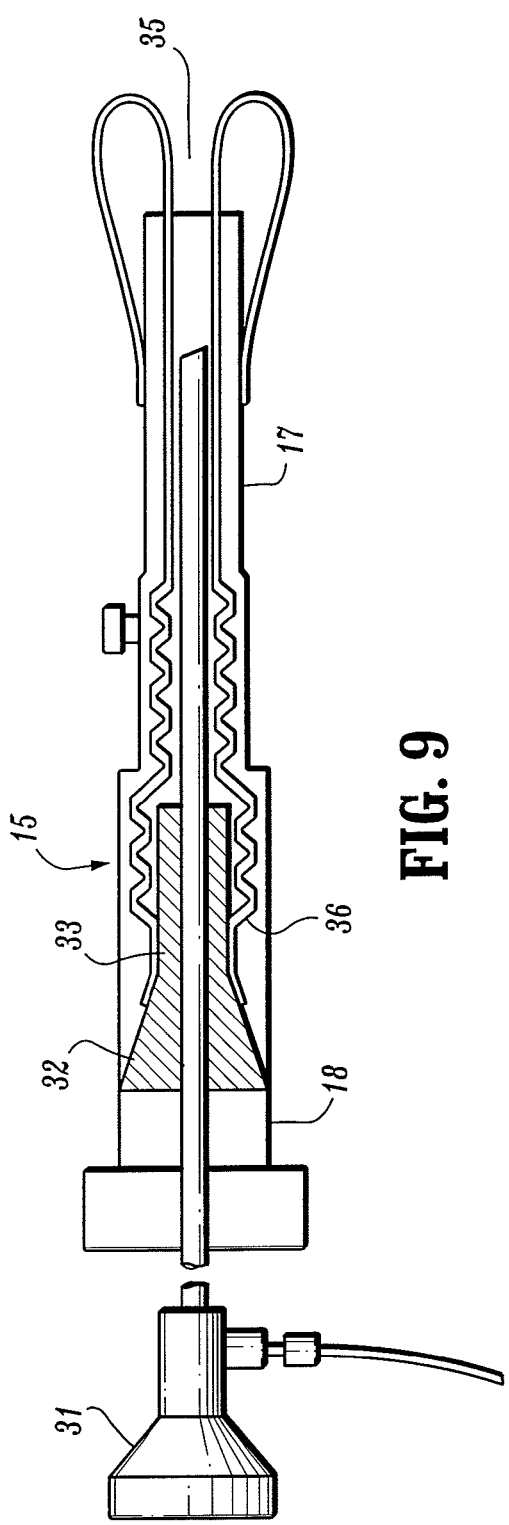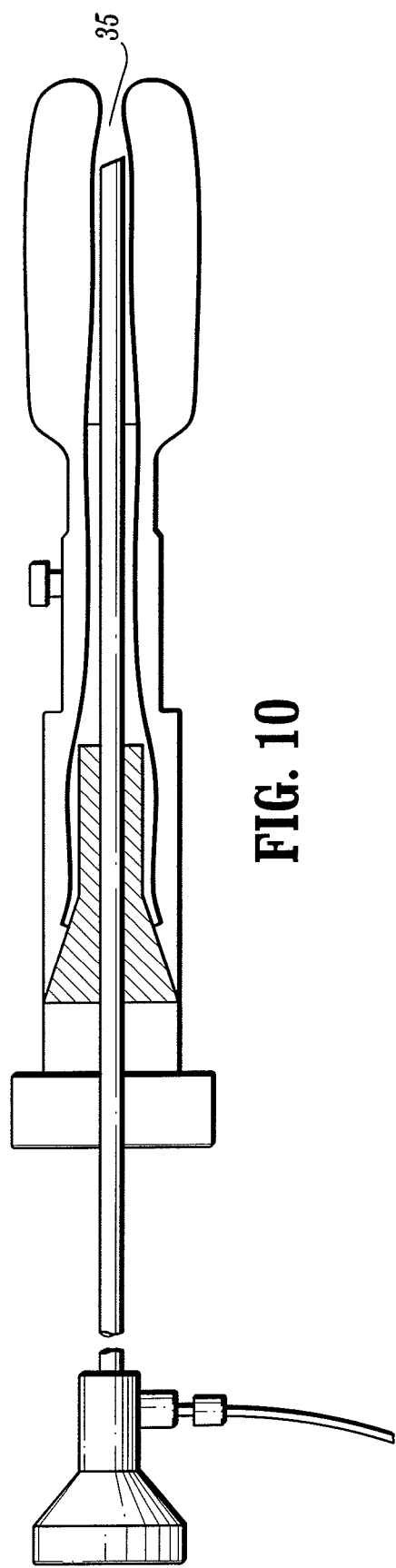
FIG. 9
FIG. 10

METHODS AND DEVICES FOR BLOOD VESSEL HARVESTING

CROSS REFERENCE TO RELATED APPLICATIONS

This application is a continuation of U.S. application Ser. No. 11/019,889, filed on Dec. 22, 2004 now U.S. Pat. No. 7,588,584, which is a divisional of U.S. application Ser. No. 10/244,330, filed on Sep. 16, 2002, now U.S. Pat. No. 6,840, 946, which is a continuation of U.S. application Ser. No. 09/520,308, filed on Mar. 7, 2000, now U.S. Pat. No. 6,451, 035, which is a continuation of U.S. application Ser. No. 09/236,266, filed on Jan. 22, 1999, now U.S. Pat. No. 6,068, 639, which is a continuation of U.S. application Ser. No. 09/145,148, filed on Sep. 1, 1998, now U.S. Pat. No. 5,899, 913, which is a continuation of U.S. application Ser. No.08/ 991,425, field on Dec. 15, 1997, now U.S. Pat. No. 5,853,417, which is a continuation of U.S. application Ser. No. 08/475, 137, filed on Jun. 7, 1995, now U.S. Pat. No. 5,730,748. The priority of these prior applications is expressly claimed and their disclosures are hereby incorporated by reference in their entirety.

FIELD OF THE INVENTION

This invention relates to methods and devices for endoscopic surgery, in particular to methods and devices for dissecting tissue to create a working space for endoscopic instruments.

BACKGROUND OF THE INVENTION

Numerous surgical procedures have been developed to replace arteries that have become blocked by disease. The aortocoronary bypass surgery is perhaps the most important of these bypass operations. The coronary arteries supply blood to the heart. As a result of aging and disease, coronary arteries may become blocked by plaque deposits, stenosis, or cholesterol. In some instances, these blockages can be treated with artherectomy, angioplasty or stent placement, and coronary bypass surgery is not required. Coronary bypass surgery is required when these other methods of treatment cannot be used or have failed to clear the blocked artery. In the coronary bypass surgery, a vein is harvested from elsewhere in the body and grafted into place between the aorta and the coronary artery beyond the point of blockage.

The coronary bypass surgery requires a length of vein or artery for the graft. It is preferred to use a vein taken from the patient undergoing the bypass surgery. The patient is a ready source of suitable veins that will not be rejected by the body after transplantation and grafting onto the aorta and coronary artery. The saphenous vein in the leg is the best substitute for small arteries such as the coronary arteries, and it is the preferred vein for use in coronary bypass surgery. This is because the saphenous vein is typically 3 to 5 mm in diameter, about the same size as the coronary arteries. Also, the venous system of the legs is sufficiently redundant so that after removal of the saphenous vein, other veins that remain in the leg are adequate to provide adequate return blood flow. The cephalic vein in the arm is an alternative that is sometimes used.

In a typical operation previously required to harvest the saphenous vein, the surgeon cut into the leg to allow access to the saphenous vein and cut the vein from the leg. To expose the vein, the surgeon makes a series of incisions from the groin to the knee or the ankle leaving one or more skin bridges along the line of the incisions. (Some surgeons make one continuous incision from the groin to the knee or ankle). Handling of the vein must be kept to a minimum, but the vein must be removed from connective tissue that requires some force to remove. After exposing the vein, the surgeon grasps it with his fingers while stripping off the surrounding tissues with dissecting scissors or other scraping instruments. The surgeon uses his fingers and blunt dissection tools to pull and lift (or mobilize) the vein from the surrounding tissue. The vein is mobilized or pulled as far as possible through each incision. To reach under the skin bridges, the surgeon lifts the skin with retractors and digs the vein free. While stripping the vein, the surgeon will encounter the various tributary veins that feed into the saphenous vein. These tributaries must be ligated and divided. To divide and ligate tributaries that lie under the skin bridges, the surgeon may need to cut one end of the saphenous vein and pull it under the skin bridge to gently pull the vein out from under the skin bridge until the tributary is sufficiently exposed so that it may be ligated and divided. When the vein has been completely mobilized, the surgeon cuts the proximal and distal ends of the vein and removes the vein from the leg. After removal, the vein is prepared for implantation into the graft site, and the long incisions made in the leg are stitched closed.

The procedure described above can be used to harvest veins for a femoral popliteal bypass, in which an occluded femoral artery is bypassed from above the occlusion to the popliteal artery above or below the knee. The procedure can also be used to harvest veins for the revascularization of the superior mesenteric artery which supplies blood to the abdominal cavity and intestines. In this case, the harvested vein is inserted between the aorta to the distal and patent (unblocked) section of the mesenteric artery. For bypass grafts of the lower popliteal branches in the calf, the procedure can be used to harvest the umbilical vein. The harvested vein can also be used for a vein loop in the arm (for dialysis) between the cephalic vein and brachial artery. The procedures may be used also to harvest veins for femoral-tibial, femora-peroneal, aorto-femoral, and iliac-femoral bypass operations and any other bypass operation.

As can be seen from the description of the harvesting operation, the harvesting operation is very traumatic in its own right. In the case of coronary artery bypass, this operation is carried out immediately before the open chest operation required to graft the harvested vein into the coronary arteries. The vein harvesting operation is often the most troublesome part of the operation. The long incisions created in the leg can be slow to heal and very painful. Complications resulting from the vein harvesting operation can also hinder the patient's recovery from the entire operation.

The method of vein harvesting presented herein is accomplished with endoscopic procedures. This allows the veins to be harvested in an operation that requires only a few small incisions. Endoscopic surgical techniques for operations such as gall bladder removal and hernia repair are now common. The surgeon performing the operation makes a few small incisions and inserts long tools, including forceps, scissors, and staplers into the incision and deep into the body. Viewing the tools through an endoscopic laparoscope, or a video display from the endoscope, the surgeon can perform all the cutting and suturing operations necessary for a wide variety of operations. The procedures are also referred to as laparoscopic surgery, minimally invasive surgery, or video-assisted surgery. References to endoscopic surgery and endoscopes below is intended to encompass all these fields, and all operations described below with reference to endoscopes can also be accomplished with laparoscopes, gastroscopes, and any other imaging devices which may be conveniently used.

Minimally invasive procedures for vein removal have been proposed. Knighton, Endoscope and Method for Vein Removal, U.S. Pat. No. 5,373,840 shows a method of cutting the saphenous vein at one end, and grasping the vein with graspers or forceps, then sliding a ring over the vein while holding it. Knighton uses a dissecting tool with an annular cutting ring, and requires that the saphenous vein be overrun or progressively surrounded with the dissecting tool and the endoscope, so that after the endoscope has been inserted as far as it will go, the entire dissected portion of the vein has been pulled in the lumen of the endoscope. As shown in FIGS. 1 and 10 of Knighton, the method requires deployment of the forceps inside the annular dissection loop, and it requires deployment of the loop and graspers inside the endoscope lumen. The blood vessel must be cut and grasped by the forceps before it can be dissected by the dissecting ring.

The method of vein harvesting presented below may use a balloon to assist in dissecting the harvested vein. An everted balloon stored inside a cannula or trocar may be inserted through one of the small incisions and inflated so that it everts out the end of the cannula and forces its way along the vein to create a tunnel. Endoscopic balloons have been used for retraction and dissecting in other applications, but not for dissection and tunneling for harvesting blood vessels. Kieturakis and Mollenauer, Apparatus and Method for Developing an Anatomic Space for Laparoscopic Procedures with Laparoscopic Implantations, U.S. Pat. No. 5,540,791 shows a balloon designed to separate the peritoneum from the overlying fascia (skin, fat, and connective tissue). This creates a working spare for laparoscopic repair of hernias: The balloons described below provide additional features making it suitable for use in endoscopic or laparoscopic vein harvesting.

It is an object of the inventions presented herein to provide methods and devices for harvesting veins with a less traumatic operation than the operations presently-used to harvest veins.

SUMMARY OF THE INVENTION

The methods and devices presented herein allow surgeons to harvest veins without making the long incisions previously required. The procedure is a minimally invasive procedure that requires just a few small incisions, one at either end of the saphenous vein. The procedure is accomplished with endoscopic or laparoscopic instruments under the guidance of an endoscope. The surgeon makes one small incision at each end of the saphenous vein. After making the incisions, the surgeon inserts a tunneling instrument or blunt dissector into one incision and advances or pushes along the saphenous vein to make a small tunnel along the saphenous vein. The surgeon then inserts the long balloon described below in the tunnel and inflates the balloon to enlarge and further propagate the tunnel. The surgeon may use the balloon to dissect the fat and skin overlying the saphenous vein away from the vein, and also to enlarge the tunnel to an appropriate size. When the tunneling is completed, the surgeon removes the balloon and seals the tunnel at both ends. The surgeon then injects carbon dioxide, nitrous oxide, or other suitable gas into the tunnel at sufficient pressure (typically 5-15 mmHg) to inflate the tunnel and create room for laparoscopic instruments. The surgeon then inserts an endoscope or laparoscope through the seal to provide a view of the procedure, and inserts an endoscopic vein harvesting device described in detail below. With the vein harvester in place, the surgeon manipulates the vein harvester to strip the connective tissue from the vein, identify and cut side branches, and remove the vein from its channel in the leg. After the vein is loosened or dissected free from its channel in the leg, the surgeon can cut the proximal and distal ends and easily pull the vein from the leg. The small skin incisions are stitched so they may heal. The small incisions heal much more readily, with fewer complications and far less pain, than the operation now in use.

The surgeon operating with the vein harvesting device has a choice of tunneling instruments. A typical blunt dissection is performed with a long stiff rod with a round tip, and the tip may be enlarged. The surgeon may also use a device referred to as a peanut, which is long rod with a soft fabric or foam tip. These devices are used to create a small tunnel, and then the balloon dissector may be inserted to enlarge the tunnel. The balloon dissector described below allows the tunneling operation to be accomplished by the balloon, thus allowing easier and less traumatic creation of the initial tunnel, and also permitting the surgeon to create the enlarged tunnel with this single device. The device may be used as an alternative to the other methods of enlarging the tunnel.

BRIEF DESCRIPTION OF THE DRAWINGS

FIG. 2 shows the balloon dissector with the balloon housed in the handle.

FIG. 3 shows the balloon dissector with the balloon in its inflated state.

FIG. 4 shows the balloon cannula with the balloon fully inflated.

FIG. 9 shows a balloon dissector with a thru-lumen.

FIG. 10 shows the balloon dissector with thru-lumen with the balloon fully inflated.

DETAILED DESCRIPTION OF THE INVENTION

Figure 1:
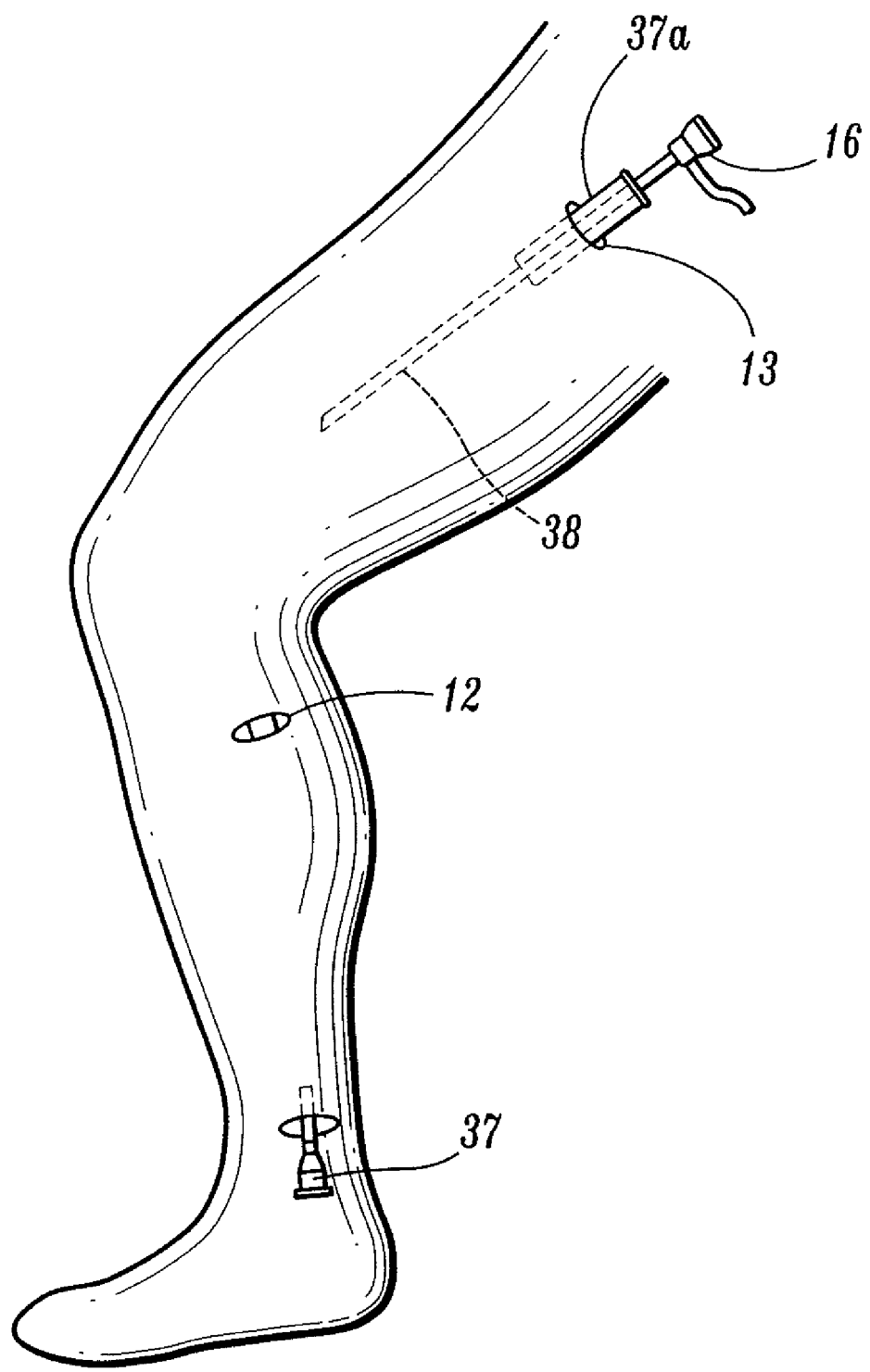
FIG. 1 is a view of the leg showing incisions necessary for harvesting the saphenous vein using the methods presented herein.

The methods and devices presented herein take advantage of laparoscopic procedures to lessen the trauma of vein harvesting operations. Instead of making an incision along or over the entire length, or essentially the entire length of the vein to be harvested, the procedure may be conducted with only a few small incisions. All that is needed is a working space large enough to allow the surgeon to use the tool and view the operation through a laparoscope. In the preferred embodiment of the method, the surgeon creates a working space under the skin and over the saphenous vein using laparoscopic techniques. The surgeon makes several small incisions to expose the saphenous vein. These incisions are referred to as cut-downs. A distal incision near the knee and a proximal incision at the groin are preferred. If the entire length of the saphenous vein is to be harvested, an additional incision can be made close to the ankle. The saphenous vein can be seen through the cut-downs. It will be apparent from the description that the use of three or four incisions used to harvest the entire saphenous vein are merely a matter of convenience, and those particularly skilled in laparoscopic procedures may require fewer incisions, and also more small incisions may be required.

After incision, the surgeon inserts a blunt tunneling tool (not shown) into one incision and pushes it along the saphenous vein towards the other incision. The tunneling creates a tunnel or channel running along the saphenous vein. The tunnel may be expanded by insertion of the balloon described herein, which can be inflated to expand or propagate the tunnel further along the saphenous vein.

FIG. 2 shows the balloon dissector or balloon trocar 15 in its uninflated state, with the balloon packed inside the device. The balloon 16 is a non-elastomeric balloon or bladder. The balloon trocar 15 comprises a balloon 16, a trocar portion 17 and a balloon housing portion 18. The trocar portion 17 is cylindrical, with a circular cross section, but may be made in oval cross section or in other cross sections. The balloon 16 is sealed to the distal tip 19 of the trocar portion 17 of the balloon trocar 15. The balloon material is wrapped over the distal tip 19 and sealed to the outside of the trocar portion 17. The balloon 16 may be sealed to the trocar 15 with adhesives, or it may be heat sealed, banded or taped (cellophane tape, such as SCOTCH™ adhesive tape, is sufficient) or sealed in any suitable manner to the trocar. The balloon 16 then extends back through the trocar, to the proximal balloon housing portion 18 of the balloon trocar 15. When used for tunneling along the saphenous vein, the balloon is approximately 60 centimeters long. The trocar or cannula is most conveniently 10-20 centimeters long, so that the excess length of the balloon is folded as shown inside the balloon housing portion of the balloon trocar. The balloon is sealed at its distal end 20, referring here to the distal end as determined when the balloon is everted outside of the balloon housing. The balloon may be formed by extrusion or by heat sealing or gluing a number of pieces of material together.

The balloon trocar 15 is fitted with an inflation port 21, which may be located anywhere on the trocar portion 17 or balloon housing 18. In FIG. 2, the inflation port is shown affixed to the balloon housing at its proximal end near the neck-down portion 22 between the balloon portion and the trocar portion. The inflation port comprises a tube establishing a pathway for liquid or gas to be injected into the balloon trocar to inflate the balloon. A convenient length of flexible tubing such as tygon tubing 23 can be used to connect the balloon to a bladder pump 24 or large syringe capable of injecting liquid or gas into the balloon housing. Sterile saline solution is the preferable inflation medium for medical applications. Alternately, air, $CO_2$, or even foam or other substances may be injected to cause inflation.

Upon injection of liquid or gas into the balloon housing, the pressure created inside the housing forces the balloon to evert out through the trocar portion of the balloon. The segment of the balloon stored in the housing portion gradually rolls forward (distally) and outside the trocar, rolling over itself and turning itself inside out, or everting, and pushing forward. As shown in FIG. 3, the balloon has everted under pressure, and the leading edge 25 pushes forward, unrolling from the inside, and advances through body tissue. Eventually the balloon completely unfolds or everts to create a long cylindrical balloon. The balloon may be folded in a variety of ways, including the fan fold shown in FIG. 3 or with accordion folds, as shown in FIG. 9, or it may be rolled inside the cannula.

Figure 6:
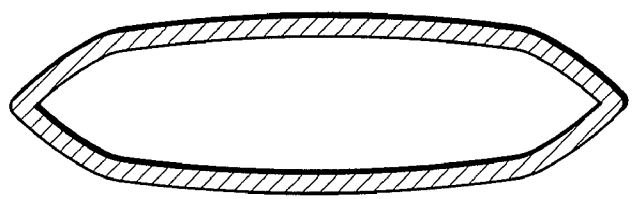
FIG. 6 shows a cross section of the inflatable membrane in its inflated state.
Figure 5:
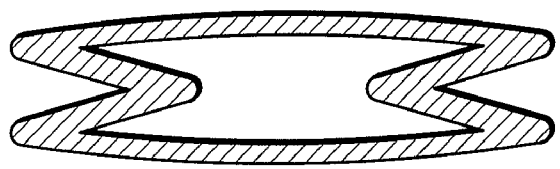
FIG. 5 shows a cross section of the inflatable membrane in its uninflated state.

The fully inflated and everted balloon is shown in FIG. 4. The inflated diameter of the balloon is more useful when it is larger than the diameter of the trocar. This allows for the creation of a tunnel that is wider than the trocar. The balloon diameter or radial cross section of the balloon may also be smaller than the diameter of the trocar, and may be adjusted to create a tunnel of any desired size. The balloon may be pleated, or folded like a brown paper bag, or folded in any other manner which facilitates eversion and packing in the housing. The cross section of the uninflated balloon along section a of FIG. 3 is shown in FIG. 5, and the cross section of the inflated balloon along cross section b of FIG. 4 is shown in FIG. 6. The balloon is preferably non-elastic, so that it will not expand uncontrollably into the softest body tissue or weakest tissue plane. Acceptable materials include polyethylene and other medical grade plastics. A slight degree of elasticity is acceptable, and even complete elasticity may be acceptable where there is no danger of the balloon expanding in an unwanted or unpredictable shape.

Figure 7:
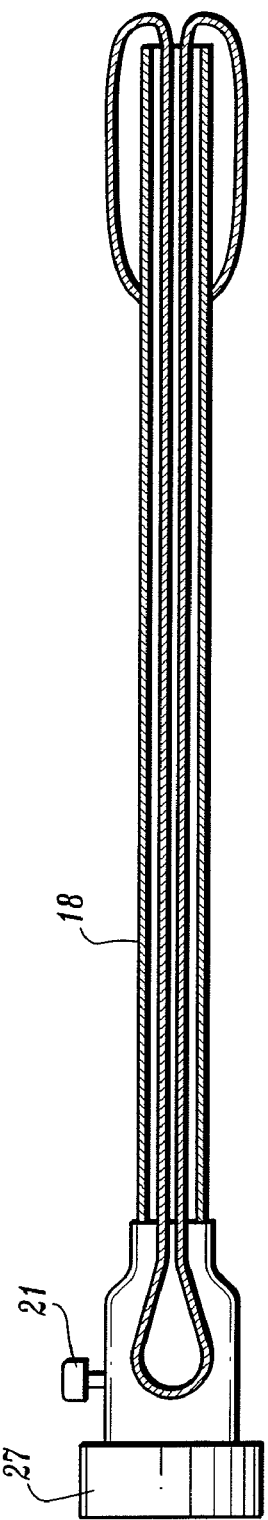
FIG. 7 shows a cross section of a simplified balloon cannula.

FIG. 7 shows an alternate embodiment of the balloon trocar in which the excess length of the balloon is stored inside a longer housing so that it need not be folded. The balloon housing 18 is longer than the balloon housing 18 shown in FIG. 2. The balloon is sealed at the distal tip of the trocar in the same manner shown in FIG. 2, and the distal end of the balloon is sealed. The inflation port 21, again, may be placed in any convenient place on the balloon trocar. The proximal end of the balloon housing is sealed by an end cap 27, which can be integrally formed with the balloon trocar. The end cap can also be removable and include a threaded cap which is screwed onto the end of the balloon housing and fitted with a gasket to prevent leakage. The end cap can also include a plug 28 which fits tightly into the balloon housing, and the plug may be provided with an O-ring 29 to help maintain the seal on the housing. Upon inflation, the balloon everts or unfolds out the distal tip of the balloon trocar. The balloon forces itself between the body tissues to be dissected or tunneled through in the same manner as describe above.

Figure 8:
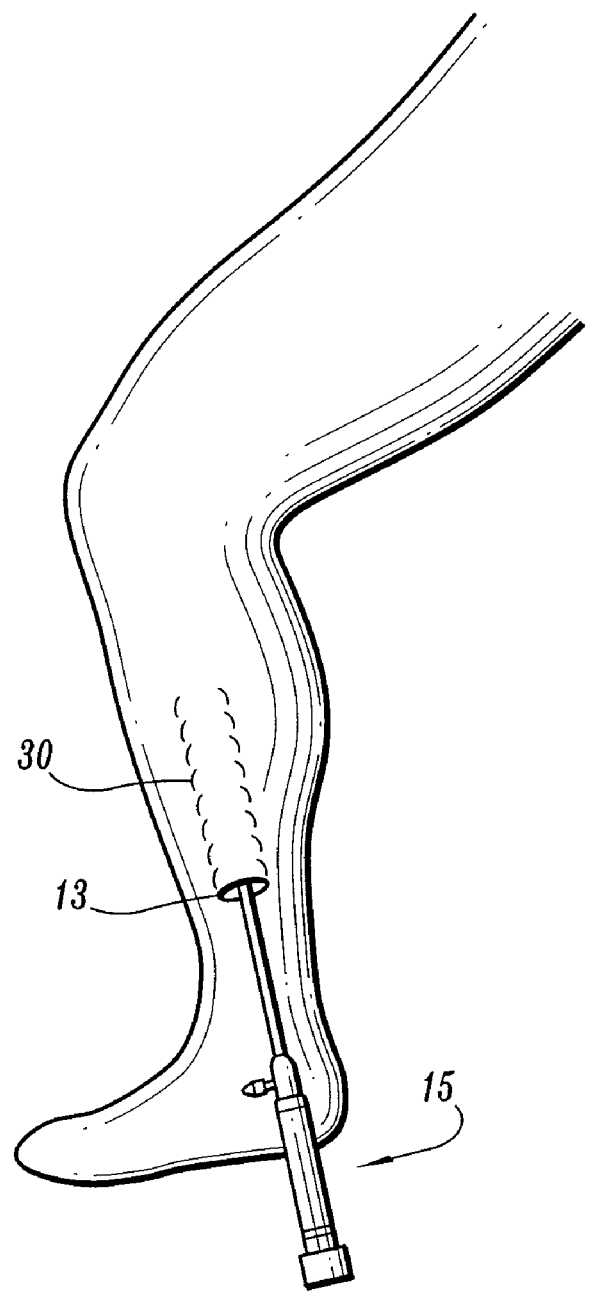
FIG. 8 shows the balloon cannula inserted in the leg of a patient.

FIG. 8 shows the balloon trocar inserted into the ankle incision or cut down 13. The surgeon inserts the balloon into the incision and points it in the direction of the tunnel that he wants to make. In the illustration, the balloon trocar is inserted as it would be if the surgeon wanted to create or enlarge a tunnel along the saphenous vein, going up the leg. Once the surgeon has put the balloon trocar in place, the balloon is ready for inflation. The surgeon can inflate the balloon and allow it to evert into the leg. The balloon will follow a tunnel previously created by the surgeon with a blunt dissecting tool, if the surgeon has chosen to create the tunnel with another tool and use the balloon to enlarge that tunnel. The balloon will also create its own tunnel, without the need to create an initial tunnel over the entire length of the saphenous vein. The surgeon can make a small starter tunnel, using a finger or tool to get the tunnel started, then the surgeon can insert the balloon and inflate it. Upon eversion or unrolling, the balloon will force its way into the leg and propagate along the tissue boundary between the saphenous vein and the fat and skin layer above the vein. Eversion and propagation of the balloon creates a tunnel over the saphenous vein, or, in medical terms, superior to the saphenous vein. As the balloon propagates along the vein, it raises the skin over the balloon, creating a bubble or blister 30 which indicates that the balloon is everting along the vein, and has not taken some errant course. As the balloon propagates up the leg, the surgeon may guide it by pushing the tip of the balloon with his finger, through the skin without puncturing the skin. In this manner, the balloon gently forces its way between the layers of body tissue and pushes them apart to form the, enlarged tunnel necessary for endoscopic or laparoscopic surgery on the saphenous vein.

The balloon dissector can be used in other procedures besides dissection for vein harvesting, and its description in that environment is intended to be illustrative of the device. The device can be used in any procedure for dissection, separating or retracting body tissue. The balloon trocar may be made in varying sizes and lengths, so that it can be used to create passageways for laparoscopic surgery. After the passage is created, whether by the balloon or other means, the balloon trocar may be used to hold passageways open to allow laparoscopic instruments to be used in front of the distal end or leading edge of the everting balloon. These instruments may be inserted through the thru-lumen of the balloon trocar, or they may be inserted through other access ports so that the balloon is used only to hold body tissue out of the way of these instruments as they are used. Additionally, the device may be used to hold an endoscope or laparoscope in a fixed and stable position within the body, so that the video display which the surgeon watches remains stable.

As described above, the balloon trocar is used for dissection or tunneling in a semi-blind manner. When used in the leg, the propagation of the balloon can be observed by watching skin rise as the balloon tunnels under the skin. Because the location of the saphenous vein is well known and its exact course through the leg can be readily determined, the surgeon can be sure that the balloon is following the intended path along the saphenous vein. In some cases, however, the surgeon may wish to observe the propagation of the balloon endoscopically or the surgeon may wish to observe various structures as the balloon everts past the structures. The everting balloon with a thru-lumen depicted in FIG. 9 can be used in this instance.

As shown in FIG. 9, the balloon trocar 15 may be constructed to allow passage of an endoscope 31 or other instrument through the balloon. The balloon housing 18 and trocar portion 17 of the device may be similar to the comparable structures shown in FIG. 2. The balloon is sealed to the distal tip of the trocar portion, and is also sealed to the proximal end of the balloon housing by sealing the balloon the sliding piston seal or sliding plunger 32. The sliding piston seal fits tightly against the inside of the balloon housing to create an air tight seal. A guide tube 33 is provided attached to the sliding piston to facilitate sliding the endoscope through the through lumen. Alternatively, in the configuration shown in FIG. 11, the balloon comprises a tube of non-elastic material with a short length of cuff rolled back at each end and folded over the proximal edge and sealing it to the outside of the balloon housing. The balloon housing may be provided with an end cap 27 to prevent backward eversion of the balloon, and the end cap may be provided with a port 34 which accommodates the endoscope. Any other suitable sealing means may be used. FIG. 10 shows the balloon in its fully extended state with the lumen large enough for an endoscope to be inserted through the inside of guide tube or mandril 33. With the balloon inflated or deflated, an endoscope can be inserted through the thru-lumen 35, as shown in FIGS. 9 and 10.

Figure 11:
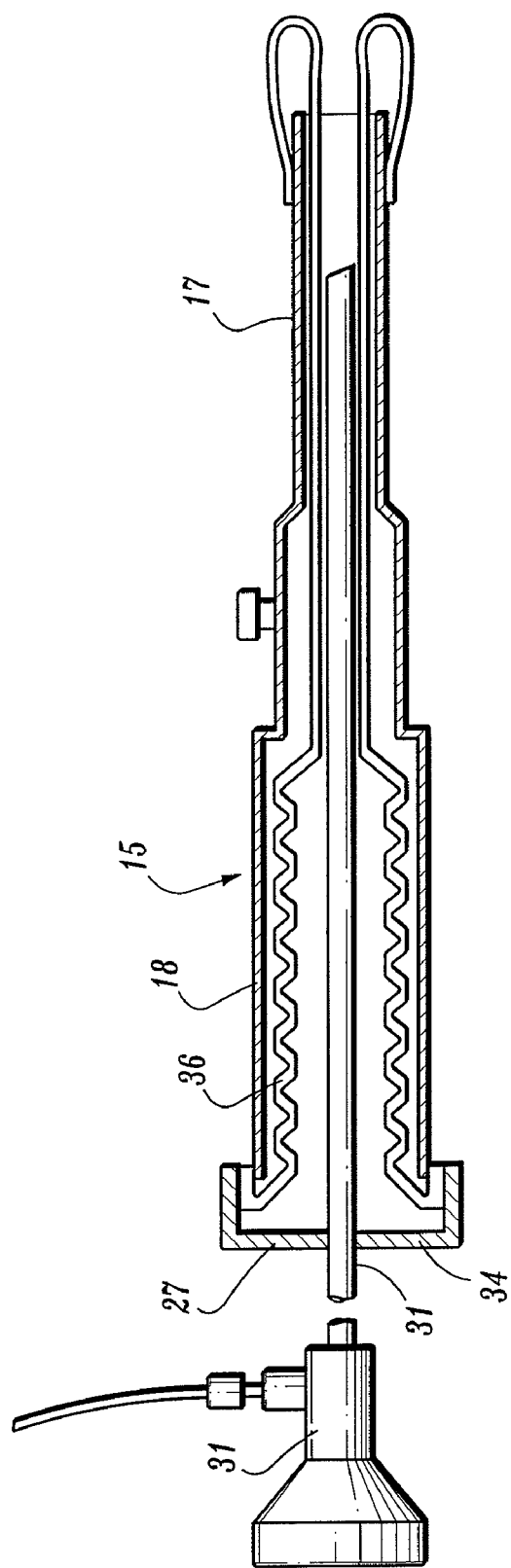
FIG. 11 shows an alternative embodiment of the balloon dissector with a thru-lumen.

Before the balloon is inflated to cause eversion which is used for tunneling or dissection or retraction of body tissue, it is folded accordion style inside the balloon housing portion of the balloon trocar. The excess length is held inside the housing in this manner until the balloon is everted under pressure. The accordion folds 36 can be made without a mandril, as shown in FIG. 11, or with a mandril 33 as shown in FIGS. 9 and 10. Alternatively, the endoscope or other instrument used within the lumen may be used as the mandril. The mandril can be integral with the end cap, or it can be mounted on a fixed or sliding plunger, annular seal, sealing ring or piston seal 32. Provision of a sliding plunger allows longer deployment of the balloon outside the trocar portion.

While in use, the balloon may be inflated and everted partially or fully to cause it to tunnel through body tissue or between tissue planes. During eversion, the endoscope can be advanced to the leading edge or everted distal end of the balloon so that the surgeon can view the body tissue as it is dissected.

Insufflation

When the tunnel is of sufficient size, the incisions may be sealed with round trocars 37 and 37a, shown in place in FIG. 1. The trocars are used to insert the various tools used in the procedure. One trocar is used to inject or infuse carbon dioxide ($CO_2$) or other gas (or liquid) into the tunnel in a procedure known as insufflation, which pressurizes the tunnel and keeps it open and expanded to make it easier to see inside the tunnel and easier to insert and manipulate an endoscope and instruments into the tunnel. Insufflation is accomplished with techniques generally known to endoscopic and laparoscopic surgeons. As can be seen in FIG. 1, the insufflation creates an inflated space 38 under the skin. An endoscope or laparoscope 16 is inserted into one of the trocars 37 or 37a, and is shown in FIG. 1 inserted into the groin incision 13 through trocar 37a. The endoscope permits the surgeon to view the tunnel, including the saphenous vein and connective tissue. The endoscope fits tightly into the trocar so a seal is accomplished between the endoscope and the trocar, and this helps maintain the pressure of the $CO_2$ gas. Also during insufflation, the vein harvesting tool may be inserted through the ankle trocar and operated to dissect and strip the vein and mobilize it. The incision may optionally be made at the knee, as indicated at item 12, or may be made at both the knee and the ankle so that the balloon dissecting devices and vein harvesting devices can be used to dissect the saphenous vein first in the thigh and then in the calf, or vice-versa.

Figure 12:
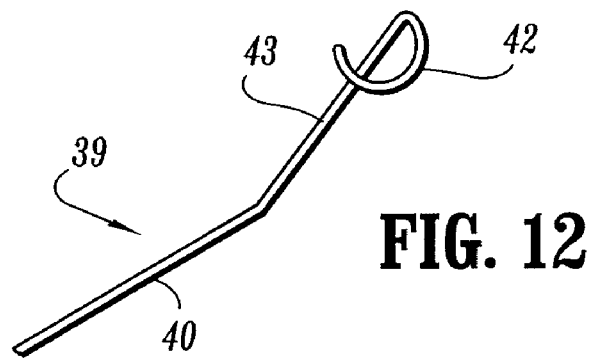
FIG. 12 shows a hooked vein harvester.

FIG. 12 shows a hooked vein harvesting tool 39 particularly suited for use in the method. The hooked vein harvesting tool 39 comprises a shaft or long slender rod 40 of stiff wire with a grip 41 on one end and a sideways hook 42 on the end. The hooked vein harvester may be made of stainless steel, plastic, or other biocompatable material such as nitinol. The long segment or shaft 40 may have an offset or crooked segment 43 to set the hook off the axis established by the shaft. The sideways hook 42 is generally perpendicular to the axis of the shaft, or, in other words, the plane in which the hooks lies perpendicular to the line established by the shaft or crooked section. Of course, the hook need not be exactly perpendicular, and maybe set at any angle which facilitates the ability to use the hook as described herein. By twisting or rotating the shaft 40, the surgeon can slip the hook under the exposed saphenous vein. The hook 42 may be provided with a pointed tip to enable it to puncture the connective tissue which covers the saphenous vein. The hook occupies an arc or radial segment of about 180° to 270° so that the saphenous vein will lie inside the hook when engaged by the hook. The diameter of the circle defined by the hooked is slightly larger than the diameter of the saphenous vein, so that the hook can be easily slipped under the saphenous vein. When the hook 42 is safely around the saphenous vein, the surgeon can separate the vein from the surrounding tissue by pulling or pushing the shaft and sliding the hook along the saphenous vein. When a side branch is encountered, the hook will be blocked by the side branch, and can be used to expose the side branch for ligation and dividing it from the saphenous vein. When the entire length of the saphenous vein has been separated from the connective tissue, the vein can be grasped with laparoscopic grippers and pulled from the leg through the groin incision 13, the knee incision 12 or the ankle incision 14.

Figure 16:
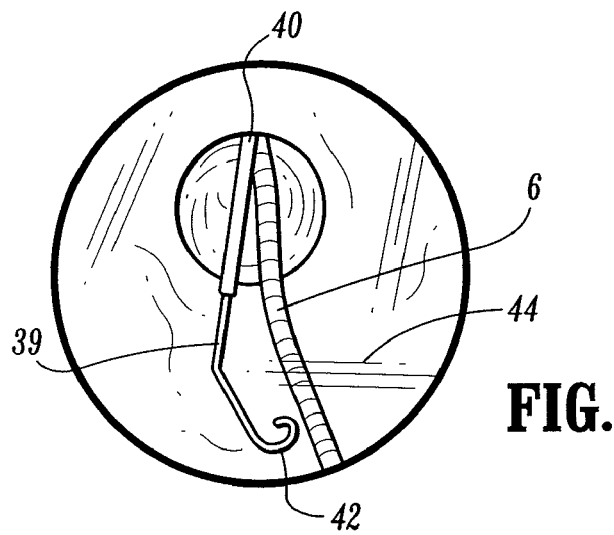
FIGS. 16-18 are laparoscopic views of the hooked vein harvester being placed around the saphenous vein.
Figure 17:
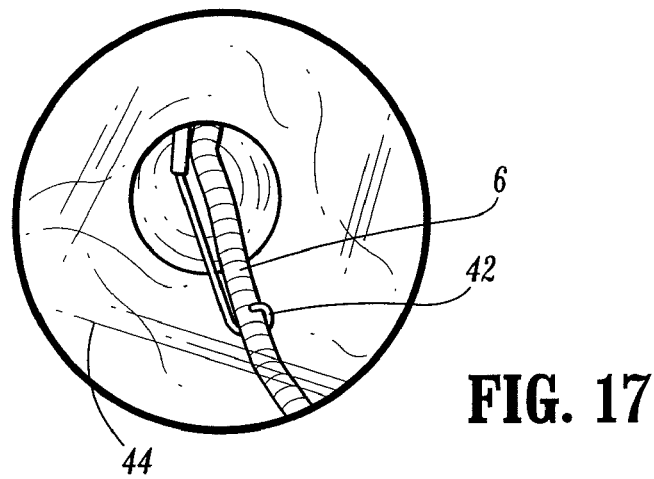
Figure 18:
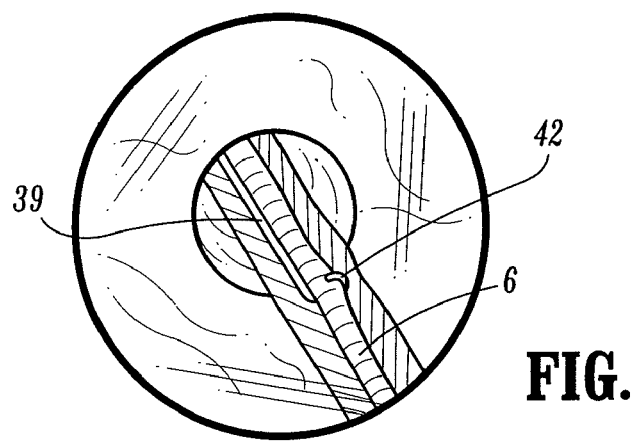
Figure 19:
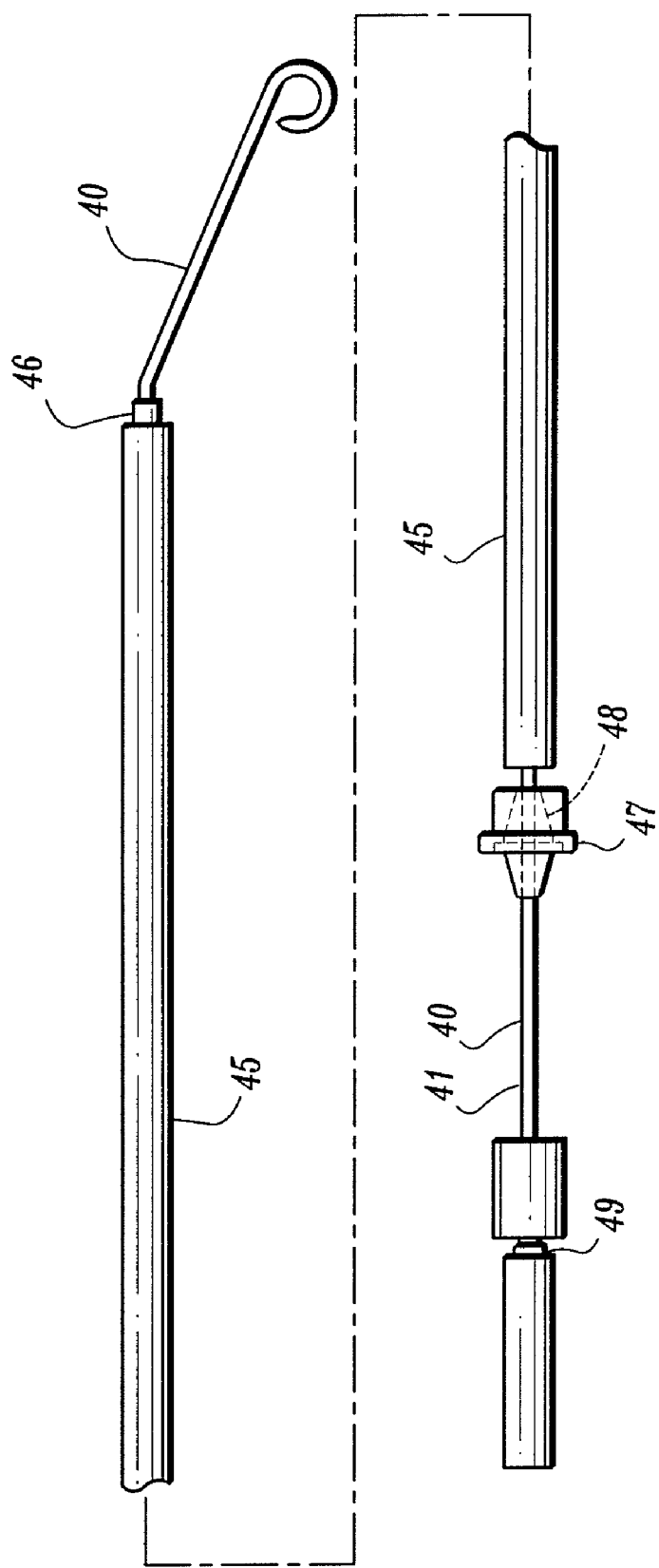
FIG. 19 shows the hooked vein harvester tool fitted with sealing tubes facilitating its use during insufflation.

FIGS. 16-18 show the use of the hooked vein harvester 39 as viewed through an endoscope inserted through the groin incision 11. The saphenous vein 6 is seen lying in its channel surrounded by connective tissue 44. The hooked vein harvester 39 is shown as it would appear when inserted from the knee incision 12. The hook 42 appears in the foreground and the shaft 40 is receding toward the far end of the tunnel. In FIG. 16, the hook 42 is in position at the upper end of the saphenous vein. In FIG. 17, the shaft has been twisted or rotated by the surgeon so that the hook is slipped under and round the saphenous vein. In FIG. 18, the surgeon has pulled the vein harvester, and perhaps rotated the hook a bit more and pulled again, and freed or dissected the saphenous vein front the connective tissue. The shaft can be manipulated to lift or mobilize the saphenous vein from the channel in which it lies. The shaft can be pushed and pulled as necessary to separate or dissect the connective tissue from the vein. Several other features of the device are provided in order to make it more suitable for use in conjunction with the trocar and the $CO_2$ insufflation. These features make it easier to deploy the vein harvester through a standard trocar with an inside diameter that is larger than the wire 40. As shown in FIG. 19 a tube 45 surrounds the wire 40 for the greater portion of its length. At the distal end of the tube, an O-ring 46 or plastic sealing ring is fixed to the inside of the tube and fits closely around the shaft or wire 40. This seal helps maintain the $CO_2$ pressure inside the tunnel so that the tunnel remains inflated or insufflated while the vein harvester is in use. At the proximal end of the tube 45, a valve assembly 47 with a duckbill valve 48 inside fits tightly into the tube 45. The valve assembly allows the wire to pass through the duckbill valve 48, and the duckbill valve closes around the wire to provide an additional seal around the wire. A second O-ring or plastic sealing ring can also be used to provide a second seal at the proximal end of the tube. To make handling of wire easier, a handle 49 can be provided on the proximal end 41 or the wire. The handle shown in FIG. 19 is removable, but a fixed handle may be provided.

The saphenous vein has a number of tributary veins that carry venous blood into it. These tributaries must be tied off and cut off of the saphenous vein before the saphenous vein can be removed. In medical terms, these tributaries must be ligated and divided. These tributaries can be readily identified with the vein harvester because the surgeon will feel the resistance while pulling and will not be able to pull the hook through a tributary vein. When a tributary is encountered, the surgeon can use standard endoscopic and laparoscopic tools to close the tributaries and cut them from the saphenous vein. The tributaries can be separated from the vein after the entire vein is stripped, or the surgeon may choose to separate them as they are encountered.

Figure 13:
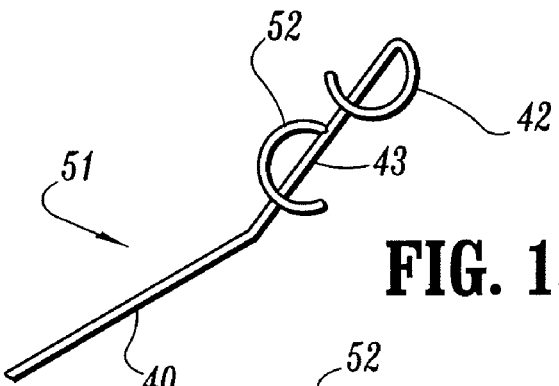
FIGS. 13 and 14 show a double-hooked vein harvester.

FIG. 13 shows a double hooked vein harvester 51 with the same shaft 40 and hook 42 at the distal end of the shaft, and a second hook 52 fixed to the shaft just a short distance before the hook 42 which is fixed at the extreme end of the shaft. This end of the shaft is referred to as the distal end because it is end that is inserted into the body. (The handle end which remains outside the body is referred to as the proximal end.) The second hook 52 is located a short distance proximal of the first hook 42 which is located at the distal tip of the shaft 40. The proximal hook or second hook 52 opposes the first hook or distal hook 42, and extends from the shaft along a plane perpendicular to the shaft. Where the first hook extends counterclockwise from the rod, the second hook extends clockwise from the rod so that the two hooks are in opposing relationship. The hook need not be exactly perpendicular, and need only be offset to a degree sufficient to allow it to engage the saphenous vein upon rotation toward the vein.

Figure 14:
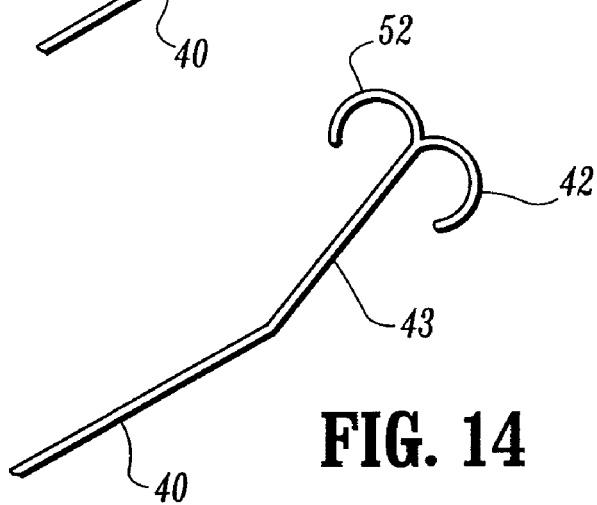

The double hooked vein harvester 51 is used in much the same manner as the hooked vein harvester 39. The first hook 42 is slipped under the saphenous vein and rotated fully so that the second hook 52 can be slipped over the saphenous vein, so that the vein is more fully surrounded by the hooks. The hooks can be made long enough to fully encircle the vein. In this case, tributary veins will obstruct the proximal hook or second hook 52 when it is pulled. When obstructed, the shaft can be rotated until the second hook is no longer obstructed by the tributary vein, and pulled until the second hook passes the tributary. The tributary will then block the distal hook, and can be passed by again rotating the shaft back to its original position until the distal hook is no longer obstructed, and the shaft 40 can be pulled until the distal hook 42 passes the tributary. Alternatively, the hooks can be made short enough so that they do not completely encircle the vein. In this manner, the hooks can be pulled more safely past tributary veins because a radial segment will remain open between the hooks. An alternative embodiment of the double hooked vein harvester may have both hooks located at the same point on the shaft and opposing each other, as shown in FIG. 14.

Figure 15:
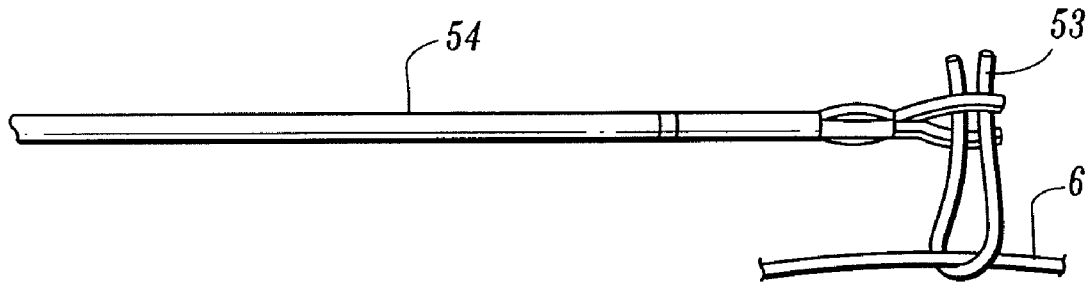
FIG. 15 shows a tube harvester.

Another device for vein harvesting is shown in FIG. 15. A soft plastic or rubber tube 53 is threaded under the saphenous vein using standard laparoscopic instruments such as laparoscopic forceps and a hooked suturing needle (not shown). After the tube has been threaded around the vein, the surgeon grasps both ends in a laparoscopic grasper 54. With the tube grasped close to the vein so that it surrounds the vein, the surgeon can pull the tube along the vein to separate the vein from its connective tissue and lift it from its channel. Tributaries are detected when the surgeon feels more resistance to pulling on the tube. The tube may be made of any material which is pliant enough to thread around the vein and pulled along the vein without injuring the vein.

Some of the advantages of the vein harvester may be beneficial during open surgery, as well as endoscopic vein harvesting.

The device and method described above has been developed in the field of vein harvesting and vascular surgery. However, it is readily apparent that the devices and methods may be used for dissecting and mobilizing other long organs of the body. Various arteries and veins must be dissected and mobilized for other operations, such as popliteal bypass, or a dialysis vein loop. In these operations, a vein must be harvested, and the sites at which the vein will be attached or amostosized must also be uncovered. The balloon dissector may also be used to gain access to any blood vessel for any type of vascular surgery. For example, the device and method described above has been developed in the field of vein harvesting and vascular surgery. However, it is readily apparent that the devices and methods may be used for dissecting and mobilizing other long organs of the body. The balloon dissector may also be used to gain access to any blood vessel for any type of vascular surgery.

The vein harvesting devices shown above may be made with a variety of materials. The methods shown may be applied to harvesting veins or arteries other than the saphenous vein and other veins mentioned above, and may be employed for harvesting veins for transplant into any area of the body. Where appropriate, the devices and methods may be used during open surgery to facilitate the removal of veins or arteries, in which case the working space is provided by the normal open surgery techniques. While the preferred embodiments of the devices and methods have been described, they are merely illustrative of the principles of the invention. Other embodiments and configurations may be devised without departing from the spirit of the inventions and the scope of the appended claims.

What is claimed:

1. A device for creating a working space in a body comprising:
   an elongate tubular member;
   a piston member disposed within the tubular member, the piston member forming a substantially fluid tight seal with an inner surface of the tubular member; and
   an expandable member disposed within the tubular member, at least a portion of a distal end of the expandable member secured to the tubular member and at least a portion of a proximal end of the expandable member secured to the piston member, the expandable member adapted to receive an inflation medium therein, the expandable member having a central lumen extending therethrough for receiving a surgical instrument.

2. The device of claim 1, wherein the expandable member is generally cylindrical when folded and stored within the tubular member.

3. The device of claim 1, wherein the expandable member maintains the central lumen upon introduction of an inflation medium into the expandable member.

4. The device of claim 1, wherein expansion of the expandable member creates a working space within the body that is accessible through the central lumen.

5. The device of claim 1, wherein the expandable member is sized and dimensioned to create a working space over a tubular organ in the body.

6. The device of claim 1, wherein the expandable member is formed from a non-elastomeric material.

7. The device of claim 1, wherein the piston member is repositionable in the tubular member such that, upon introduction of an inflation medium into the expandable member, the expandable member everts from the tubular member and the piston member remains stationary while the expandable member is partially everted.

8. The device of claim 1 further comprising:
   a member housing portion of the tubular member capable of storing the expandable member within the tubular member, the expandable member capable of being turned inside out and stored with the member housing, and capable of everting out the distal end of the tubular member upon introduction of an inflation medium.

9. The device of claim 8, wherein the expandable member is stored in the member housing in a folded condition and is stored therein to facilitate gradual unfolding during eversion.

10. The device of claim 9, wherein the expandable member is folded in a fan fold manner.

11. The device of claim 9, wherein the expandable member is folded in an accordion like manner.

12. The device of claim 9, wherein the expandable member is stored in the member housing in a rolled condition.

13. The device of claim 1, wherein the expandable member is longer than the tubular member and folded to fit within the tubular member.

* * * * *